(12) United States Patent
Williamson et al.

(10) Patent No.: US 10,363,181 B2
(45) Date of Patent: *Jul. 30, 2019

(54) PATIENT POSITION DETECTION FOR PATIENT SUPPORT APPARATUS

(71) Applicant: Hill-Rom Services, Inc., Batesville, IN (US)

(72) Inventors: Rachel L. Williamson, Batesville, IN (US); Charles A. Lachenbruch, Batesville, IN (US); Timothy J. Receveur, Guilford, IN (US); Robert M. Zerhusen, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 620 days.

This patent is subject to a terminal disclaimer.

(21) Appl. No.: 15/133,692

(22) Filed: Apr. 20, 2016

(65) Prior Publication Data

US 2016/0250088 A1    Sep. 1, 2016

Related U.S. Application Data

(63) Continuation of application No. 13/769,975, filed on Feb. 19, 2013, now Pat. No. 9,358,168.

(Continued)

(51) Int. Cl.
*A61G 7/00* (2006.01)
*A61G 7/05* (2006.01)
(Continued)

(52) U.S. Cl.
CPC .............. *A61G 7/015* (2013.01); *A47C 27/10* (2013.01); *A61G 7/001* (2013.01); *A61G 7/002* (2013.01);
(Continued)

(58) Field of Classification Search
CPC .... A61G 13/08; A61G 13/04; A61G 2203/44; A61G 7/053; A61G 7/05769;
(Continued)

(56) References Cited

U.S. PATENT DOCUMENTS 5,276,432 A   1/1994   Travis
5,526,543 A   6/1996   DiMatteo
(Continued)

FOREIGN PATENT DOCUMENTS

EP    1 997 467    12/2008

OTHER PUBLICATIONS

European search report from EP 13 18 2951, dated Mar. 20, 2014 (7 pages).

*Primary Examiner* — Robert G Santos
*Assistant Examiner* — Myles A Throop
(74) *Attorney, Agent, or Firm* — Barnes & Thornburg LLP

(57) ABSTRACT

A patient support apparatus includes a patient support surface to support a patient. The patient support surface has at least one air bladder that is inflated and/or deflated to achieve a turn assist function and/or a therapy function of the patient support surface. A graphical user interface (GUI) is configured to receive user inputs from a caregiver to initiate the turn assist or therapy functions. The patient support apparatus has control circuitry coupled to the GUI. The GUI is controlled by the control circuitry to display information indicating that the patient is improperly positioned on the patient support surface for either the turn assist function or the therapy function. Alternatively or additionally, the control circuitry indicates that the patient is improperly positioned for raising a head section of a bed frame.

20 Claims, 11 Drawing Sheets

Related U.S. Application Data

(60) Provisional application No. 61/696,449, filed on Sep. 4, 2012.

(51) Int. Cl.

| | | |
|---|---|---|
| *A47C 27/10* | (2006.01) | |
| *A61G 7/002* | (2006.01) | |
| *A61G 7/012* | (2006.01) | |
| *A61G 7/015* | (2006.01) | |
| *A61G 7/018* | (2006.01) | |
| *A61G 7/057* | (2006.01) | |
| *G16H 40/63* | (2018.01) | |
| *G06F 3/0481* | (2013.01) | |
| *G06F 3/0484* | (2013.01) | |
| *G06F 19/00* | (2018.01) | |

(52) U.S. Cl.
CPC .............. *A61G 7/012* (2013.01); *A61G 7/018* (2013.01); *A61G 7/05769* (2013.01); *A61G 7/05792* (2016.11); *G06F 3/04817* (2013.01); *G06F 3/04842* (2013.01); *G06F 19/00* (2013.01); *G16H 40/63* (2018.01); *A61G 7/0507* (2013.01); *A61G 2203/16* (2013.01); *A61G 2203/20* (2013.01); *A61G 2203/32* (2013.01); *A61G 2203/34* (2013.01); *A61G 2203/44* (2013.01); *A61G 2203/46* (2013.01)

(58) Field of Classification Search
CPC ................ A61G 7/005; A61G 2200/32; A61H 2201/0142; A61H 2201/501; A61H 2201/5046; A61H 2201/5058; A61B 5/1115; A61B 2562/0247; A61B 5/0002; A61B 6/04; A61B 6/0407; A61J 2015/008
USPC ..................................... 5/615, 715, 600, 706
See application file for complete search history.

(56) References Cited

U.S. PATENT DOCUMENTS

| | | | |
|---|---|---|---|
| 5,611,096 A | 3/1997 | Bartlett et al. | |
| 5,771,511 A | 6/1998 | Kummer et al. | |
| 5,806,115 A | 9/1998 | Brown | |
| 5,975,081 A | 11/1999 | Hood et al. | |
| 6,021,533 A | 2/2000 | Ellis et al. | |
| 6,067,019 A | 5/2000 | Scott | |
| 6,115,860 A | 9/2000 | Vrzalik | |
| 6,208,250 B1 | 3/2001 | Dixon et al. | |
| 6,351,678 B1 | 2/2002 | Borders | |
| 6,353,950 B1 | 3/2002 | Bartlett et al. | |
| 6,536,056 B1 | 3/2003 | Vrzalik et al. | |
| 6,584,628 B1 | 7/2003 | Kummer et al. | |
| 6,611,979 B2 | 9/2003 | Welling et al. | |
| 6,658,680 B2 | 12/2003 | Osborne et al. | |
| 6,691,346 B2 | 2/2004 | Osborne et al. | |
| 6,819,254 B2 | 11/2004 | Riley | |
| 6,892,405 B1 | 5/2005 | Dimitriu et al. | |
| 6,957,461 B2 | 10/2005 | Osborne et al. | |
| 7,191,482 B2 | 3/2007 | Romano et al. | |
| 7,253,366 B2 | 8/2007 | Bhai | |
| 7,260,860 B2 | 8/2007 | Chambers et al. | |
| 7,296,312 B2 | 11/2007 | Menkedick et al. | |
| 7,319,386 B2 | 1/2008 | Collins, Jr. et al. | |
| 7,409,735 B2 | 8/2008 | Kramer et al. | |
| 7,418,751 B1 | 9/2008 | Bartlett et al. | |
| 7,437,787 B2 | 10/2008 | Bhai | |
| 7,464,605 B2 | 12/2008 | Douglas et al. | |
| 7,469,436 B2 | 12/2008 | Meyer et al. | |
| 7,538,659 B2 | 5/2009 | Ulrich et al. | |
| 7,557,718 B2 | 7/2009 | Petrosenko et al. | |
| 7,565,710 B2 | 7/2009 | Chambers et al. | |
| 7,805,784 B2 | 10/2010 | Lemire et al. | |
| 7,861,334 B2 | 1/2011 | Lemire et al. | |
| 7,962,981 B2 | 6/2011 | Lemire et al. | |
| 7,973,666 B2 | 7/2011 | Petrosenko et al. | |
| 7,975,335 B2 | 7/2011 | O'Keefe et al. | |
| 8,006,333 B2 | 8/2011 | Genaro et al. | |
| 8,108,957 B2 | 2/2012 | Richards et al. | |
| 8,117,701 B2 | 2/2012 | Bobey et al. | |
| 8,201,292 B2 | 6/2012 | Dionne et al. | |
| 8,393,026 B2 | 3/2013 | Dionne et al. | |
| 8,413,271 B2 | 4/2013 | Blanchard et al. | |
| 8,466,801 B2 | 6/2013 | Hayes et al. | |
| 9,013,313 B2 | 4/2015 | Paine | |
| 9,358,168 B2 | 6/2016 | Williamson et al. | |
| 2002/0196141 A1 | 12/2002 | Boone et al. | |
| 2003/0208847 A1 | 11/2003 | Vrzalik et al. | |
| 2004/0177445 A1* | 9/2004 | Osborne | A61G 7/0528 5/600 |
| 2006/0075559 A1 | 4/2006 | Skinner et al. | |
| 2006/0101581 A1 | 5/2006 | Blanchard et al. | |
| 2007/0210917 A1 | 9/2007 | Collins, Jr. et al. | |
| 2008/0172789 A1 | 7/2008 | Elliot et al. | |
| 2008/0235872 A1 | 10/2008 | Newkirk et al. | |
| 2009/0013470 A1 | 1/2009 | Richards et al. | |
| 2009/0212925 A1 | 8/2009 | Schuman, Sr. et al. | |
| 2009/0212926 A1 | 8/2009 | Du et al. | |
| 2009/0217080 A1 | 8/2009 | Ferguson et al. | |
| 2009/0237264 A1* | 9/2009 | Bobey | A61G 7/05776 340/815.69 |
| 2009/0313758 A1* | 12/2009 | Menkedick | A61G 7/0528 5/618 |
| 2011/0068928 A1 | 3/2011 | Riley et al. | |
| 2011/0277242 A1 | 11/2011 | Dionne et al. | |
| 2012/0016281 A1 | 1/2012 | Richards et al. | |
| 2012/0089419 A1 | 4/2012 | Huster et al. | |
| 2013/0006151 A1* | 1/2013 | Main | A61B 5/103 600/587 |
| 2013/0317393 A1* | 11/2013 | Weiss | G06F 19/3418 600/587 |
| 2013/0340168 A1 | 12/2013 | Meyer et al. | |
| 2014/0059770 A1 | 3/2014 | Williamson et al. | |
| 2014/0323816 A1* | 10/2014 | Soderberg | A61G 7/015 600/300 |

\* cited by examiner

PATIENT POSITION DETECTION FOR PATIENT SUPPORT APPARATUS

CROSS-REFERENCE TO RELATED APPLICATIONS

This application is a continuation of U.S. application Ser. No. 13/769,975, which was filed Feb. 19, 2013, now U.S. Pat. No. 9,358,168, which claims the benefit, under 35 U.S.C. § 119(e), of U.S. Provisional Application No. 61/696,449, which was filed Sep. 4, 2012, and each of which is hereby incorporated by reference herein.

BACKGROUND

The present disclosure relates to patient support apparatuses such as hospital beds. More particularly, the present disclosure relates to patient support apparatuses having surfaces or mattresses with air bladders that are inflated or deflated to achieve turn assist or therapeutic functions.

Hospital beds having patient support surfaces with a turn assist feature are known. Turn assist involves turning a patient toward the left side or the right side for an extended period of time so that a caregiver can more easily perform a task such as changing a wound dressing or changing bed linens. Hospital beds that have therapy features are also known. For example, in contrast to turn assist, rotation therapy involves alternately and repeatedly turning a patient from side-to-side by inflating and/or deflating bladders on a right side and a left side of a mattress. Rotation therapy is sometimes referred to as continuous lateral rotation therapy (CLRT). Other therapies associated with mattresses include low air loss therapy, percussion and/or vibration therapy, alternating pressure therapy, and wave mode therapy such as Hill-Rom's OPTIREST™ feature, just to name a few.

It is desirable for a patient to be properly positioned on a mattress when the turn assist function is operated or when a therapy function is operated. If the patient is not properly positioned on the mattress, the overall efficacy of the function or therapy may be degraded or compromised. The known prior art mattress systems rely on a caregiver's ability to visually determine whether or not a patient is properly positioned on a mattress prior to initiating a turn assist function or a therapeutic function of the mattress. It is not uncommon for patients to inadvertently shift toward a foot end of a hospital bed of the type having a bed frame with movable mattress support sections. This is because when a head section of the bed frame is raised to place a patient in a sitting up position, for example, the patient has a tendency to slide down the head section toward the foot end of the bed such that, when the head section is lowered back down again, the patient remains shifted toward the foot end of the bed. Then, when one or more caregivers pull a patient back up in bed, they may pull the patient too far toward the head end of the bed. Accordingly, there is room for improvement in connection with providing information to caregivers as to whether a patient is or is not properly positioned on a mattress.

SUMMARY

An apparatus, system, or method may comprise one or more of the features recited in the appended claims and/or the following features which, alone or in any combination, may comprise patentable subject matter:

A patient support apparatus may include a patient support surface to support a patient. The patient support surface may have at least one air bladder that either inflated or deflated or both to achieve at least one of a turn assist function and a therapy function of the patient support surface. The patient support apparatus may also have a graphical user interface (GUI) that may be configured to receive user inputs from a caregiver to initiate the turn assist function and the therapy function. The patient support apparatus may further have control circuitry that may be coupled to the GUI. The GUI may be controlled by the control circuitry to display information indicating that the patient is improperly positioned on the patient support surface for the turn assist function and the therapy function.

According to this disclosure, the information indicating that the patient is improperly positioned may include, for example, information indicating that the patient is shifted too far toward at least one of the head end and the foot end of the patient support surface. The information indicating that the patient is shifted too far toward at least one of the head end and the foot end of the patient support surface may include one or more of the following: (i) a text box with a message conveying the information, (ii) a pictorial representation of a patient lying on the patient support surface too close to the at least one of the head end and foot end, and (iii) a hip position icon that is color coded, such as being color coded yellow or red depending upon the amount that the patient's position deviates from the proper position. In some embodiments, the hip position icon may be positioned over a pictorial representation of the patient lying on the patient support surface.

In some embodiments, the turn assist function or the therapy function initiated by the caregiver may proceed automatically despite the improper position of the patient on the patient support surface. It is contemplated that one or more caregivers may take corrective action to move the patient to the proper position while the function operates in such embodiments. In other embodiments, the turn assist function or the therapy function initiated by the caregiver may be suspended, including not even being started, until after the caregiver selects a first icon on the GUI to ignore the information indicating that the patient is improperly positioned. If the caregiver selects the first icon, the function will proceed to operate. The GUI may also display a second icon that may be selected by the caregiver to abort the turn assist function or the therapy function altogether.

According to some embodiments, before the information indicating that the patient is improperly positioned on the patient support surface is displayed on the GUI, the GUI may display a patient information icon that must be selected by the caregiver. The patient information icon may flash on the GUI, for example, in response to the caregiver attempting to initiate the turn assist function or the therapy function. After the caregiver selects the patient information icon, the information indicating that the patient is improperly positioned on the patient support surface, such as that mentioned above, may appear on the GUI.

According to this disclosure, the patient support apparatus may further include a bed frame that supports the patient support surface. The bed frame may include a foot board. In some embodiments, the GUI and control circuitry may be included in a housing that may be supported on the foot board, such as being hung on the footboard or attached to a bracket on the footboard. In other embodiments, the bed frame may include a siderail and the GUI may be mounted to the siderail. The control circuitry may be carried by the siderail or elsewhere on the bed frame in such embodiments.

The bed frame that supports the patient support surface may also carry a plurality of sensors. In some embodiments, such sensors may be used to determine a weight of the patient supported on the patient support surface or may be used to determine a position of the patient on the patient support surface. Each sensor of the plurality of sensors may include a load cell, a force sensitive resistor (FSR) element, a piezoelectric material or element, a capacitive sensor, or an optical sensor, just to name a few. If load cells are used, they may include strain gages or capacitors, for example. Alternatively or additionally, the patient support surface may have a plurality of patient support bladders and a plurality of sensors, such as pressure sensors or other types of sensors, that may be used to determine a position of the patient on the patient support surface based on signals from the sensors that may be indicative as to which of the plurality of bladders the patient is atop.

The information indicating that the patient is improperly positioned on the patient support surface may be displayed on the GUI prior to the caregiver using the user inputs to initiate the turn assist function or the therapy function. The GUI may also be controlled by the control circuitry to display information indicating that the patient is properly positioned on the patient support surface. Thus, the patient position information may be among the default information that is displayed on the GUI on a home screen. In other embodiments, the information indicating whether the patient is properly positioned or improperly positioned is not normally displayed on the GUI but appears after certain user inputs are selected by a caregiver. In some embodiments, the information indicating whether the patient is properly positioned or improperly positioned may include information regarding the patient's position in the lateral direction of the patient support surface.

Alternatively or additionally, a patient support apparatus may include a patient support structure to support a patient. The patient support structure may be considered to have a head end and a foot end. The patient support structure may have a head section that supports a torso of a patient and that may be movable between a raised position supporting the patient in a sitting up position and a lowered position supporting the patient in a lying down position. The patient support apparatus may also have a set of user inputs that may be configured to receive input from a caregiver to initiate the movement of the head section between the raised and lowered positions. The set of user inputs may include a graphical user interface (GUI). Control circuitry of the patient support apparatus may be coupled to the GUI. The GUI may be controlled by the control circuitry to display information indicating that the patient is improperly positioned on the patient support structure for the movement of the head section toward the raised position.

In some embodiments, the information indicating that the patient is improperly positioned includes may include one or more of the following: (i) a text box with a message conveying the information, (ii) a pictorial representation of a patient lying on the patient support surface too close to the at least one of the head end and foot end, and (iii) a hip position icon that is color coded. The movement of the head section toward the raised position may be suspended until after the caregiver selects a first icon on the GUI to ignore the information indicating that the patient is improperly positioned. Alternatively, the movement of the head section toward the raised position may be prevented altogether until after the patient is moved to a proper position on the patient support structure.

According to this disclosure, the patient support structure may include a bed frame that, in turn, may include a siderail. The GUI may be mounted to the siderail. In some embodiments, the bed frame may have a plurality of sensors that may be used to determine a weight of the patient and that may be used to determine a position of the patient on the patient support surface. The information indicating that the patient is improperly positioned may be displayed on the GUI prior to the caregiver using the user inputs to initiate the raising of the head section. The GUI also may be controlled by the control circuitry to display information indicating that the patient is properly positioned on the patient support surface. The set of user inputs may further include a plurality of buttons spaced from the GUI. At least one button of the plurality of buttons may be used to initiate movement of the head section toward the raised position.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
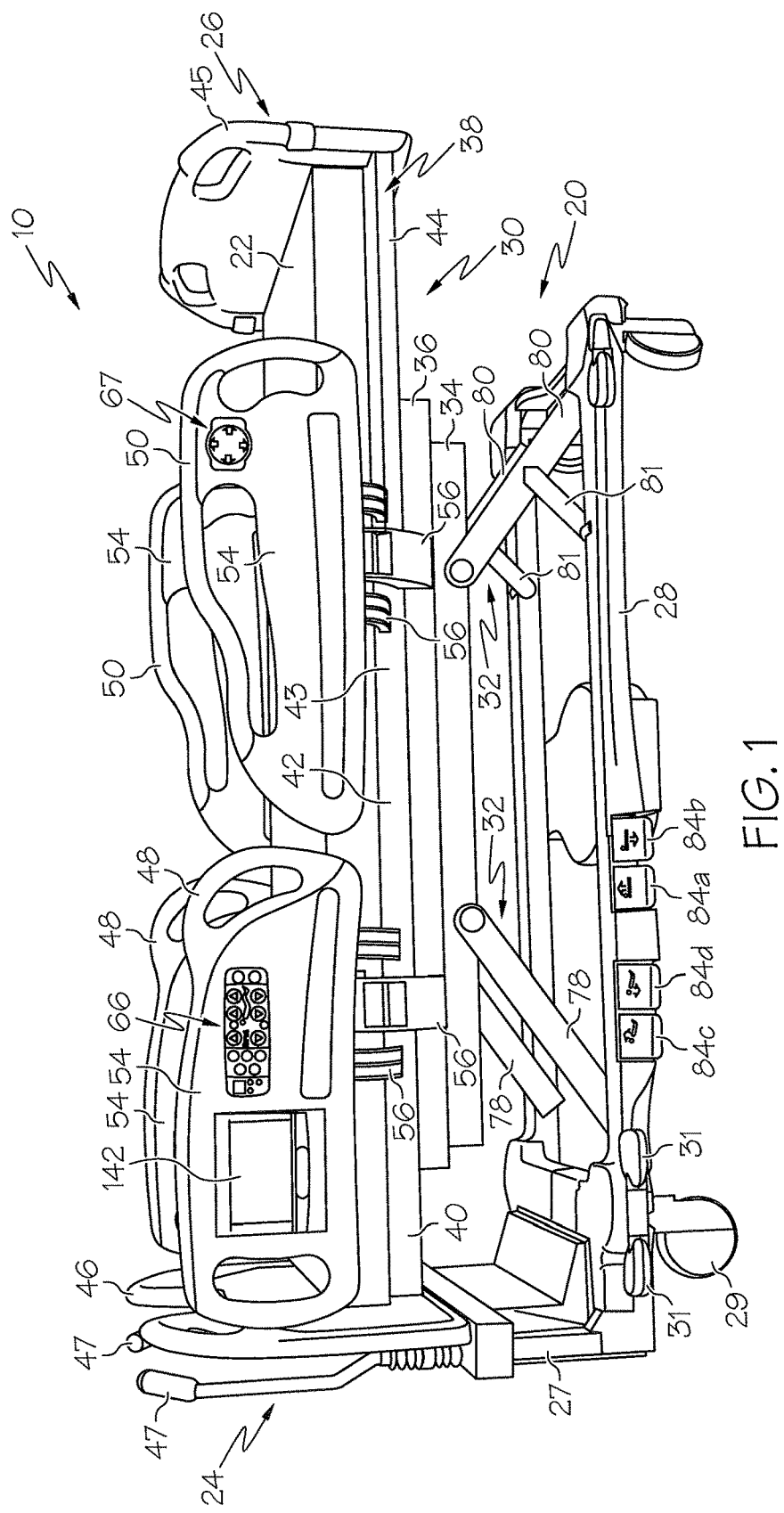
FIG. 1 is a perspective view of a hospital bed having a graphical user interface (GUI) or display screen coupled to a siderail of the hospital bed.

A patient support apparatus, such as illustrative hospital bed 10, includes a patient support structure such as a frame 20 that supports a surface or mattress 22 as shown in FIG. 1. Mattress 22 is sometimes referred to herein as patient support surface 22 or just surface 22. Thus, according to this disclosure a bed frame, a mattress or both are examples of things considered to be within the scope of the term "patient support structure." However, this disclosure is applicable to other types of patient support apparatuses and other patient support structures, including other types of beds, surgical tables, examination tables, stretchers, and the like. As will be described below in further detail, a graphical user interface (GUI) 142 of bed 10 is operable to view data or information regarding a position of a patient on bed 10 and to alert a caregiver to reposition the patient prior to a turn assist function being performed and/or prior to a therapy function being performed.

Referring again to FIG. 1, frame 20 of bed 10 includes a base 28, an upper frame assembly 30 and a lift system 32 coupling upper frame assembly 30 to base 28. Lift system 32 is operable to raise, lower, and tilt upper frame assembly 30 relative to base 28. Bed 10 has a head end 24 and a foot end 26. Hospital bed 10 further includes a footboard 45 at the foot end 26 and a headboard 46 at the head end 24. Illustrative bed 10 includes a pair of push handles 47 coupled to an upstanding portion 27 of base 28 at the head end 24 of bed 10. Headboard 46 is coupled to upstanding portion 27 of base 28 as well. Footboard 45 is coupled to upper frame assembly 30. Base 28 includes wheels or casters 29 that roll along a floor (not shown) as bed 10 is moved from one location to another. A set of foot pedals 31 is coupled to base 31 and is used to brake and release casters 29.

Illustrative hospital bed 10 has four siderail assemblies coupled to upper frame assembly 30 as shown in FIG. 1. The four siderail assemblies include a pair of head siderail assemblies 48 (sometimes referred to as head rails) and a pair of foot siderail assemblies 50 (sometimes referred to as foot rails). Each of the siderail assemblies 48, 50 is movable between a raised position, as shown in FIG. 1, and a lowered position (not shown but well-known to those skilled in the art). Siderail assemblies 48, 50 are sometimes referred to herein as siderails 48, 50. Each siderail 48, 50 includes a barrier panel 54 and a linkage 56. Each linkage 56 is coupled to the upper frame assembly 30 and is configured to guide the barrier panel 54 during movement of siderails 48, 50 between the respective raised and lowered positions. Barrier panel 54 is maintained by the linkage 56 in a substantially vertical orientation during movement of siderails 48, 50 between the respective raised and lowered positions.

Upper frame assembly 30 includes a lift frame 34, a weigh frame 36 supported with respect to lift frame 34, and a patient support deck 38. Patient support deck 38 is carried by weigh frame 36 and engages a bottom surface of mattress 22. Patient support deck 38 includes a head section 40, a seat section 42, a thigh section 43 and a foot section 44 in the illustrative example as shown in FIG. 1 and as shown diagrammatically in FIG. 2. Sections 40, 43, 44 are each movable relative to weigh frame 36. For example, head section 40 pivotably raises and lowers relative to seat section 42 whereas foot section 44 pivotably raises and lowers relative to thigh section 43. Additionally, thigh section 43 articulates relative to seat section 42. Also, in some embodiments, foot section 44 is extendable and retractable to change the overall length of foot section 44 and therefore, to change the overall length of deck 38. For example, foot section 44 includes a main portion 45 and an extension 47 in some embodiments as shown diagrammatically in FIG. 2.

In the illustrative embodiment, seat section 42 is fixed in position with respect to weigh frame 36 as patient support deck 38 moves between its various patient supporting positions including a horizontal position, shown in FIG. 1, to support the patient in a supine position, for example, and a chair position (not shown) to support the patient in a sitting up position. In other embodiments, seat section 42 also moves relative to weigh frame 36, such as by pivoting and/or translating. Of course, in those embodiments in which seat section 42 translates along upper frame 42, the thigh and foot sections 43, 44 also translate along with seat section 42. As bed 10 moves from the bed position to the chair position, foot section 44 lowers relative to thigh section 43 and shortens in length due to retraction of the extension 47 relative to main portion 45. As bed 10 moves from the chair position to the bed position, foot section 44 raises relative to thigh section 43 and increases in length due to extension of the extension relative to main portion 45. Thus, in the chair position, head section 40 extends upwardly from weigh frame 36 and foot section extends downwardly from thigh section 43.

Figure 2:
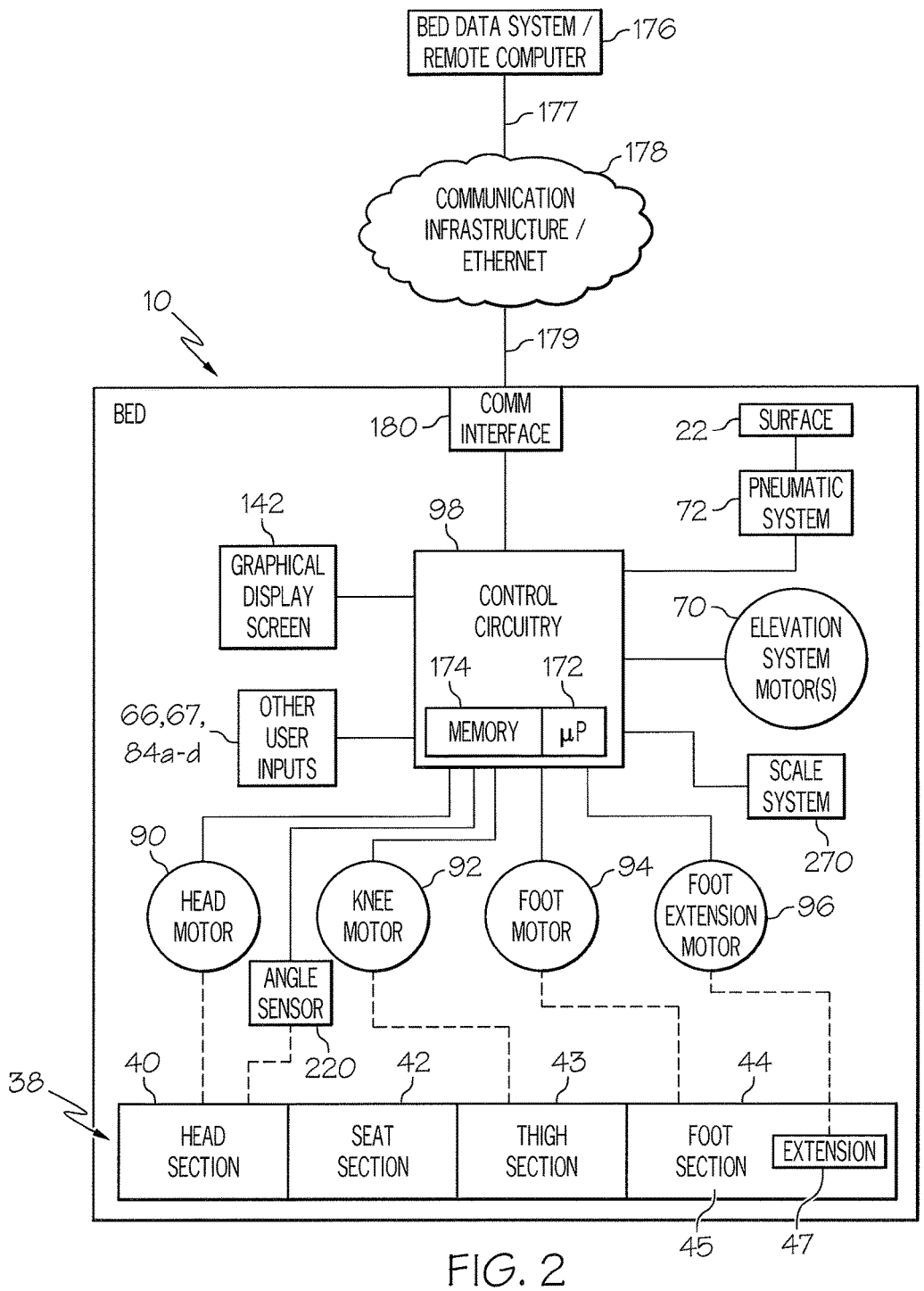
FIG. 2 is a block diagram showing electrical circuitry of the hospital bed and showing a remote computer coupled to the hospital bed via communication infrastructure.

As shown diagrammatically in FIG. 2, bed 10 includes a head motor or actuator 90 coupled to head section 40, a knee motor or actuator 92 coupled to thigh section 43, a foot motor or actuator 94 coupled to foot section 44, and a foot extension motor or actuator 96 coupled to foot extension 47. Motors 90, 92, 94, 96 may include, for example, an electric motor of a linear actuator. In those embodiments in which seat section 42 translates along upper frame 30 as mentioned above, a seat motor or actuator (not shown) is also provided. Head motor 90 is operable to raise and lower head section 40, knee motor 92 is operable to articulate thigh section 43 relative to seat section 42, foot motor 94 is operable to raise and lower foot section 44 relative to thigh section 43, and foot extension motor 96 is operable to extend and retract extension 47 of foot section 44 relative to main portion 44 of foot section 44.

In some embodiments, bed 10 includes a pneumatic system 72 that controls inflation and deflation of various air bladders or cells of mattress 22. The pneumatic system 72 is represented in FIG. 2 as a single block but that block 72 is intended to represent one or more air sources (e.g., a fan, a blower, a compressor) and associated valves, manifolds, air passages, air lines or tubes, pressure sensors, and the like, as well as the associated electric circuitry, that are typically included in a pneumatic system for inflating and deflating air bladders of mattresses of hospital beds.

The various bladders of patient support surface 22 may include one or more bladders that turn the patient to the patient's left side and one or more bladder that turn the patient to the patient's right side. Such bladders may be referred to as left turn bladder(s) and right turn bladder(s). These bladders are not shown in the present application but are well-known to those skilled in the art. The inflation and/or deflation of the left turn and right turn bladders may be done on a one-time basis to achieve a turn assist function of bed 10 or may done alternately and repeatedly through multiple cycles to achieve a rotation therapy function of bed 10.

Alternatively or additionally, the various bladders of surface 22 may also include a plurality of patient support bladders. In some embodiments, the patient support bladders may be situated above the left and right turn assist bladders, if any, and in other embodiments, the patient support bladders may be situated below the left and right turn assist bladders, if any. The patient support bladders of surface 22 may be inflated and deflated to achieve alternating therapy or wave therapy if desired. In some embodiments, the patient support bladder may be low air loss bladders to provide low air loss therapy to the patient. In other embodiments, a low air loss topper may be provided as a part of surface 22 to achieve the low air loss therapy function. Alternatively or additionally, further bladders may be provided as part of mattress 22 to achieve percussion therapy or vibration therapy or both. Each of U.S. Pat. Nos. 8,108,957; 7,975,335; 7,469,436; 7,260,860; 7,191,482; 6,584,628; and 6,021,533 is hereby expressly incorporated by reference herein to the extent that it is not inconsistent with the present disclosure which shall control as to any inconsistencies and each includes one or more examples of various types of surfaces having a turn assist function or one or more of the various therapy functions mentioned above. According to this disclosure, the surfaces disclosed in these patents are suitable for use as surface 22 or as alternatives to surface 22. Of course, these patents disclose just a few examples of the types of surfaces that may be used on bed 10.

As also shown diagrammatically in FIG. 2, lift system 32 of bed 10 includes one or more elevation system motors or actuators 70, which in some embodiments, comprise linear actuators with electric motors. Thus, actuators 70 are sometimes referred to herein as motors 70. Alternative actuators or motors contemplated by this disclosure include hydraulic cylinders and pneumatic cylinders, for example. The motors 70 of lift system 32 are operable to raise, lower, and tilt upper frame assembly 30 relative to base 28. In the illustrative embodiment, one of motors 70 is coupled to, and acts upon, a set of head end lift arms 78 and another of motors 70 is coupled to, and acts upon, a set of foot end lift arms 80 to accomplish the raising, lowering and tilting functions of upper frame 30 relative to base 28. Guide links 81 are coupled to base 28 and to lift arms 80 in the illustrative example as shown in FIG. 1. Lift system of bed 10 is substantially similar to the lift system of the VERSACARE® bed available from Hill-Rom Company, Inc. Other aspects of bed 10 are also substantially similar to the VERSACARE® bed and are described in more detail in U.S. Pat. Nos. 6,658,680; 6,611,979; 6,691,346; 6,957,461; and 7,296,312, each of which is hereby expressly incorporated by reference herein to the extent that it is not inconsistent with the present disclosure which shall control as to any inconsistencies.

In the illustrative example, bed 10 has four foot pedals 84a, 84b, 84c, 84d coupled to base 28 as shown in FIG. 1. Foot pedal 84a is used to raise upper frame assembly 30 relative to base 28, foot pedal 84b is used to lower frame assembly 30 relative to base 28, foot pedal 84c is used to raise head section 40 relative to frame 36, and foot pedal 84d is used to lower head section 40 relative to frame 36. In other embodiments, foot pedals 84a-d are omitted.

Each siderail 48 includes a first user control panel 66 coupled to the outward side of the associated barrier panel 54 and each siderail 50 includes a second user control panel 67 coupled to the outward side of the associated barrier panel 54. Controls panels 66, 67 include various buttons that are used by a caregiver (not shown) to control associated functions of bed 10. For example, control panel 66 includes buttons that are used to operate head motor 90 to raise and lower the head section 40, buttons that are used to operate knee motor to raise and lower the thigh section, and buttons that are used to operate motors 70 to raise, lower, and tilt upper frame assembly 30 relative to base 28. In the illustrative embodiment, control panel 67 includes buttons that are used to operate motor 94 to raise and lower foot section 44 and buttons that are used to operate motor 96 to extend and retract foot extension 47 relative to main portion 45. In some embodiments, the buttons of control panels 66, 67 comprise membrane switches.

As shown diagrammatically in FIG. 2, bed 10 includes control circuitry 98 that is electrically coupled to motors 90, 92, 94, 96 and to motors 70 of lift system 32. Control circuitry 98 is represented diagrammatically as a single block 98 in FIG. 6, but control circuitry 98 in some embodiments comprises various circuit boards, electronics modules, and the like that are electrically and communicatively interconnected. Control circuitry 98 includes one or more microprocessors 172 or microcontrollers that execute software to perform the various bed control functions and algorithms described herein. Thus, circuitry 98 also includes memory 174 for storing software, variables, calculated values, and the like as is well known in the art.

As also shown diagrammatically in FIG. 2, a user inputs block represents the various user inputs such as buttons of control panels 66, 67 and pedals 84a-d, for example, that are used by the caregiver or patient to communicate input signals to control circuitry 98 of bed 10 to command the operation of the various motors 70, 90, 92, 94, 96 of bed 10, as well as commanding the operation of other functions of bed 10 such as turn assist or therapy functions of surface 22. Bed 10 includes at least one graphical user input (GUI) or display screen 142 coupled to a respective siderail 48 as shown in FIG. 1. Display screen 142 is coupled to control circuitry 98 as shown diagrammatically in FIG. 2. In some embodiments, two GUI's 142 are provided and are coupled to respective siderails 48. Alternatively or additionally, one or more GUI's are coupled to siderails 50 and/or to one or both of the headboard 46 and footboard 45. Thus, it is contemplated by this disclosure that a GUI 142 may be coupled to any of barriers 45, 46, 48, 50 of bed 10. Alternatively or additionally, GUI 142 is provided on a hand-held device such as a pod or pendant that communicates via a wired or wireless connection with control circuitry 98. Further alternatively or additionally, GUI 142 as well as some or all of control circuitry 98 is carried by a housing 99 that attaches to footboard 45 as depicted in a pictorial representation or icon 110 that appears on GUI 142 as shown in FIGS. 3-9. In some embodiments, an air source such a blower or pump or compressor is also carried by housing 99 along with associated pneumatic circuitry such as manifolds, valves, conduits, and so forth.

Control circuitry 98 receives user input commands, sometimes referred to herein as simply "user inputs," from GUI 142 when display screen 142 is activated. The user input commands control various functions of bed 10 such as controlling the pneumatic system 72 and therefore, the surface functions of surface 22. In some embodiments, the input commands entered on GUI 142 also control the functions of one or more of motors 70, 90, 92, 94, 96 but this need not be the case. In some embodiments, input commands entered on the user interface 142 also control functions of a scale system 270, which is discussed in more detail below. Various examples of the various alternative or additional functions of bed 10 that are controlled by GUI 142 in various embodiments can be found in U.S. Patent Application Publication Nos. 2012/0089419 A1, 2008/0235872 A1 and 2008/0172789 A1, each of which is hereby incorporated by reference herein to the extent that it is not inconsistent with the present disclosure which shall control as to any inconsistencies.

In some embodiments, control circuitry 98 of bed 10 communicates with a remote computer device 176 via communication infrastructure 178 such as an Ethernet of a healthcare facility in which bed 10 is located and via communications links 177, 179 as shown diagrammatically in FIG. 2. Infrastructure 178 may be operated according to, for example, the IEEE 802.3 (wired Ethernet) standard and/or the IEEE 802.11 (wireless Ethernet) standard. Computer device 176 is sometimes simply referred to as a "computer" or a "server" herein. Remote computer 176 may be part of a bed data system, for example. One example of a bed data system is shown and described in U.S. application Ser. No. 13/487,460 which was filed Jun. 4, 2012, which was titled "System and Method of Bed Data Aggregation, Normalization, and Communication to Third Parties," published as U.S. Patent Application Publication No. 2012/0316892 A1, and which is hereby incorporated herein by reference to the extent that it is not inconsistent with the present disclosure which shall control as to any inconsistencies. Alternatively or additionally, it is within the scope of this disclosure for circuitry 98 of bed 10 to communicate with other computers such as those included as part of an electronic medical records (EMR) system, a nurse call system, a physician ordering system, an admission/discharge/transfer (ADT) system, or some other system used in a healthcare facility in other embodiments, although this need not be the case. Ethernet 178 in FIG. 2 is illustrated diagrammatically and is intended to represent all of the hardware and software that comprises a network of a healthcare facility.

In the illustrative embodiment, bed 10 has a communication interface or port 180 which provides bidirectional communication via link 179 with infrastructure 178 which, in turn, communicates bidirectionally with computer 176 via link 177. Link 179 is a wired communication link in some embodiments and is a wireless communications link in other embodiments. Thus, communications link 179, in some embodiments, comprises a cable that connects bed 10 to a wall mounted jack that is included as part of a bed interface unit (BIU) or a network interface unit (NIU) of the type shown and described in U.S. Pat. Nos. 7,538,659 and 7,319,386 and in U.S. Patent Application Publication Nos. 2009/0217080 A1, 2009/0212925 A1 and 2009/0212926 A1, each of which is hereby expressly incorporated by reference herein to the extent that it is not inconsistent with the present disclosure which shall control as to any inconsistencies. In other embodiments, communications link 179 comprises wireless signals sent between bed 10 and a wireless interface unit or a wireless access point of the type shown and described in U.S. Patent Application Publication No. 2007/0210917 A1 which is hereby expressly incorporated by reference herein to the extent that it is not inconsistent with the present disclosure which shall control as to any inconsistencies. Thus, communications link 177 comprises one or more wired links and/or wireless links as well, according to this disclosure.

Figure 3:
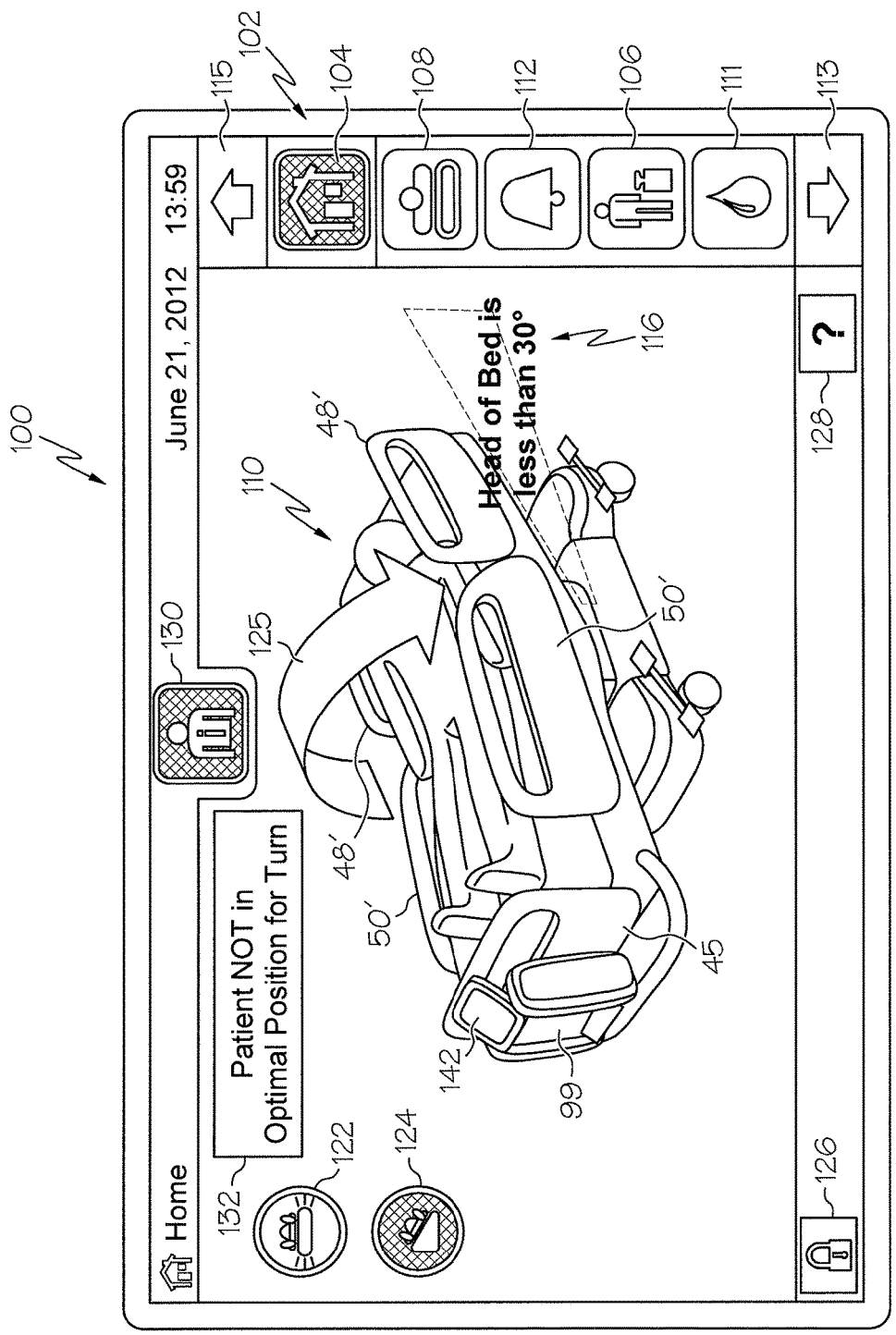
FIG. 3 is a screen shot showing a home screen after a caregiver has initiated a turn assist function of the bed, a curved arrow indicating the turn assist function is currently being operated, and the home screen having a message in a text box indicating that a patient is not in an optimal position for the turn assist function.

Referring now to FIG. 3, a home screen 100 of bed 10 that appears on GUI 142 in response to GUI 142 being awakened out of a non-interaction mode or screen saver mode includes a menu 102 of icons for navigating to other screens. With regard to awakening GUI 142 from the non-interaction mode, see U.S. application Ser. No. 13/360,846 which was filed Jan. 30, 2012, which is titled "Graphical Caregiver Interface with Swipe to Unlock Feature," and which is hereby expressly incorporated by reference herein to the extent that it is not inconsistent with the present disclosure which shall control as to any inconsistencies. Menu 102 includes a home icon (sometimes referred to herein as a "button") 104, a scale icon 106, a mattress set up icon 108, a moisture control icon 110, and an alarm icon 112. Because home screen 100 is being shown on GUI 142, the corresponding home icon 104 is highlighted in FIG. 3, as indicated by the cross hatching on icon 104.

Icons 106, 108, 111, 112 are selectable by the user to navigate to one or more screens associated with those icons to gain access to bed data and to control features or functions of bed 10. For example, in some embodiments, selection of icon 106 results in a scale control screen being displayed on GUI 142 and that has one or more icons to permit the user to do one or more of the following: set a tare weight for the scale system, select whether pounds (lb) or kilograms (kg) are to be the units of measure for the patient's weight, enter data for use in calculation of the patient's BMI, or to take a weight reading. Selection of icon 108 results in a screen that permits the user to control surface operations such as, for example, maximum inflate, turn assist left, turn assist right, therapy modes, and normal mode. Selection of icon 108, therefore, results in the user being able to navigate to screens to control therapy functions of mattress 22 such as, for example, continuous lateral rotation therapy, alternating pressure therapy, percussion and/or vibration therapy, and low air loss or microclimate management functions. Selection of icon 111 results in a screen that shows information about moisture levels in the mattress and displays controls to permit a user to select desired temperature and humidity thresholds or targets for a low air loss topper, for example. Thus, pneumatic system 72 may have a temperature sensor and a humidity sensor along with heating/cooling elements to control air temperature of the air delivered to surface 22 and may have a variable speed blower the speed of which is controllable to move air through a low air loss topper to maintain the humidity below the selected humidity threshold.

A down arrow icon 113 appears at the bottom of menu 102 beneath icon 111 and is selected to scroll downwardly to reveal other icons (not shown) of menu 102. An up arrow icon 115 appears near the top of menu 102 just above the home icon 104 and is selected to scroll upwardly to reveal additional icons (not shown) of menu 102. Screen 100 also has a bed icon or indicia 110 that includes head angle data 116 as shown in FIG. 3. In the illustrative example, head angle data 116 indicates that the head section 40 of bed 10 has been lowered to a position having an angle less than 30°. In some embodiments, the position of the siderails 48', 50' of bed icon 110 matches the position of actual siderails 48, 50 of bed 10. Thus, if one of siderails 48, 50 is lowered, then icon 110 will show the corresponding siderail 48', 50' in a lowered position on home screen 100.

In the illustrative example, screen 100 also has a pair information icon including a surface status icon 122 that indicates the state of operation of the surface such as normal, maximum inflate, left turn assist, right turn assist, rotation left, rotation center, rotation right, percussion, vibration, OPTIREST™ mode (e.g., a mode in which zones of the mattress such as the head, seat thigh, and foot zones, are sequentially reduced in pressure one zone at a time to provide a wave effect for the patient), seat deflate, and sleep mode. The other information icon in FIG. 3 is a turn assist icon 124 that, in the illustrative example, is highlighted to indicate that surface 22 of bed 10 is having its turn assist function operated. A curved arrow 125 is also displayed over icon 110 to show that the turn assist function is being operated.

Screen 100 further has a lock icon 126 that is selected to dim the GUI 142 and lock the GUI 142 from use in a non-interaction mode. Icon 126 is selected, for example, when the caregiver intends to leave bed 10 and go elsewhere or when the caregiver intends to lean over the siderail 48 to which GUI 142 is coupled, so that inadvertent contact with GUI 142 will not result in inadvertent button selections. Also on screen 100 is a help icon 128 which is selected to obtain help on GUI 142 regarding the operation of bed 10 or surface 22 and a patient information icon or button 130 which, in the illustrative example of FIG. 3, is highlighted to indicate that a patient's position on surface 22 is not the optimal position for the turn assist function which is being operated. A text box 132 also appears on screen 100 and includes the text "Patient NOT in Optimal Position for Turn." Thus, the highlighting of icon 130, such as by color coding of yellow or red or any other desired color, and the message in text box 132 serves to alert a caregiver that the patient on bed 10 should be repositioned on surface 22. It should be noted that the term "Optimal Position" in the message of box 132 refers to a range of areas that correspond to proper positions for the patient on surface 22. Once the patient is outside of the range or area of proper positions, the patient is then considered to be in an improper position.

Figure 4:
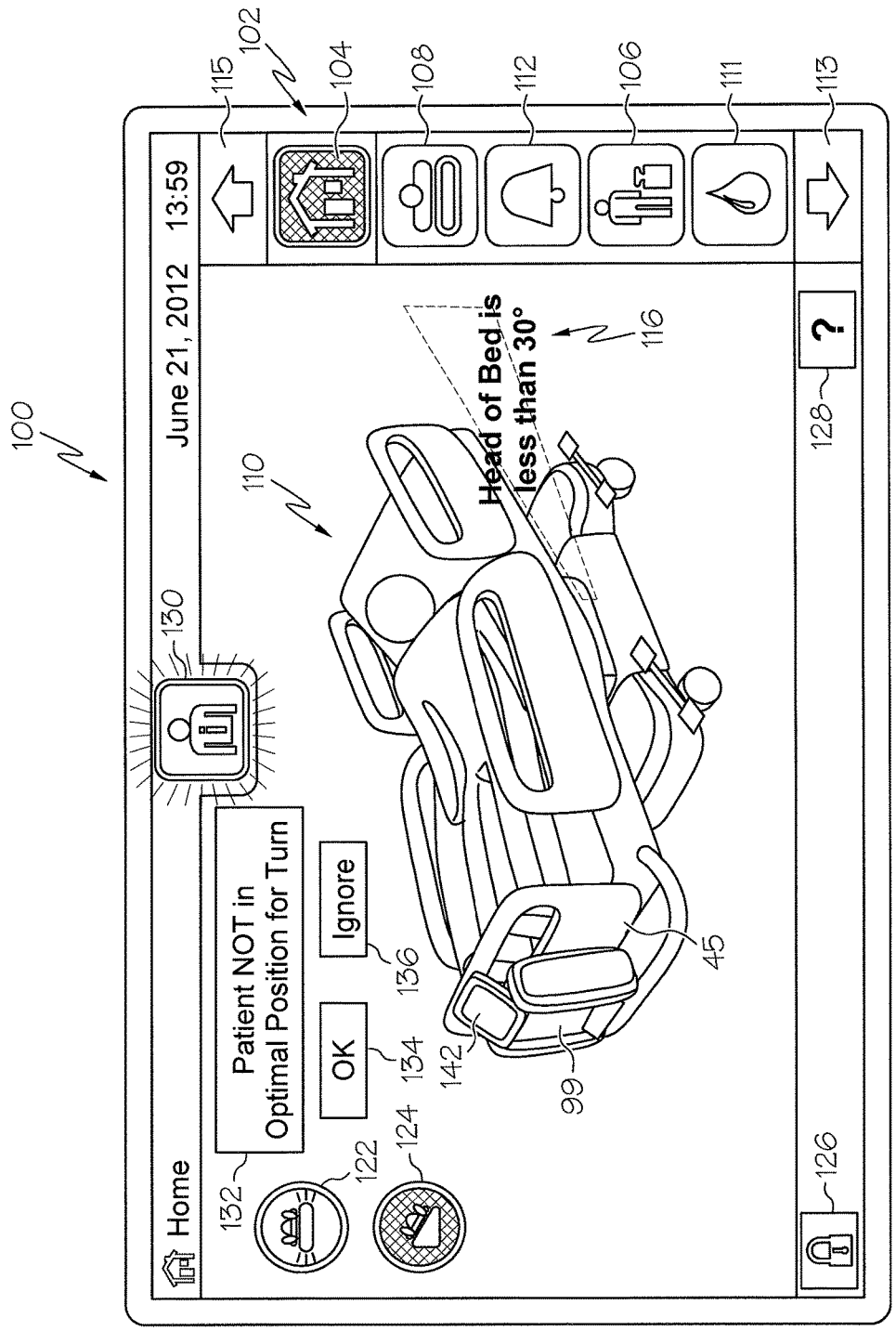
FIG. 4 is a screen shot showing an alternative home screen after a caregiver has attempted to initiate the turn assist function of the bed, a block of text indicating that the patient is not in an optimal position, an OK button or icon which is selected to abort the turn assist operation, and an Ignore button or icon which is selected to activate the turn assist function even though the patient is not in an optimal position.

Referring now to FIG. 4, an alternative home screen 100 is shown after a caregiver has attempted to initiate the turn assist function of 10 bed as indicated by icon 124 being highlighted. However, in the FIG. 4 embodiment, because the patient is not in the proper position on surface 22, the turn assist function is suspended or blocked from operating. Text box 132 appears to alert the caregiver that the patient is not in an optimal position. However, instead of highlighting icon 130 in the FIG. 4 embodiment, icon 130 flashes as suggested by the lines radiating outwardly from icon 130 in FIG. 4. Also, an OK button or icon 134 is provided on screen 100 and is selected by the caregiver to abort the turn assist operation altogether. An Ignore button or icon 136 is provided on screen 100 and is selected to activate the turn assist function even though the patient is not in an optimal position. It is also worth noting that in the FIG. 4 variant, icon 110 has been modified slightly to graphically represent that the patient has shifted toward a foot end of bed 10.

Figure 5A:
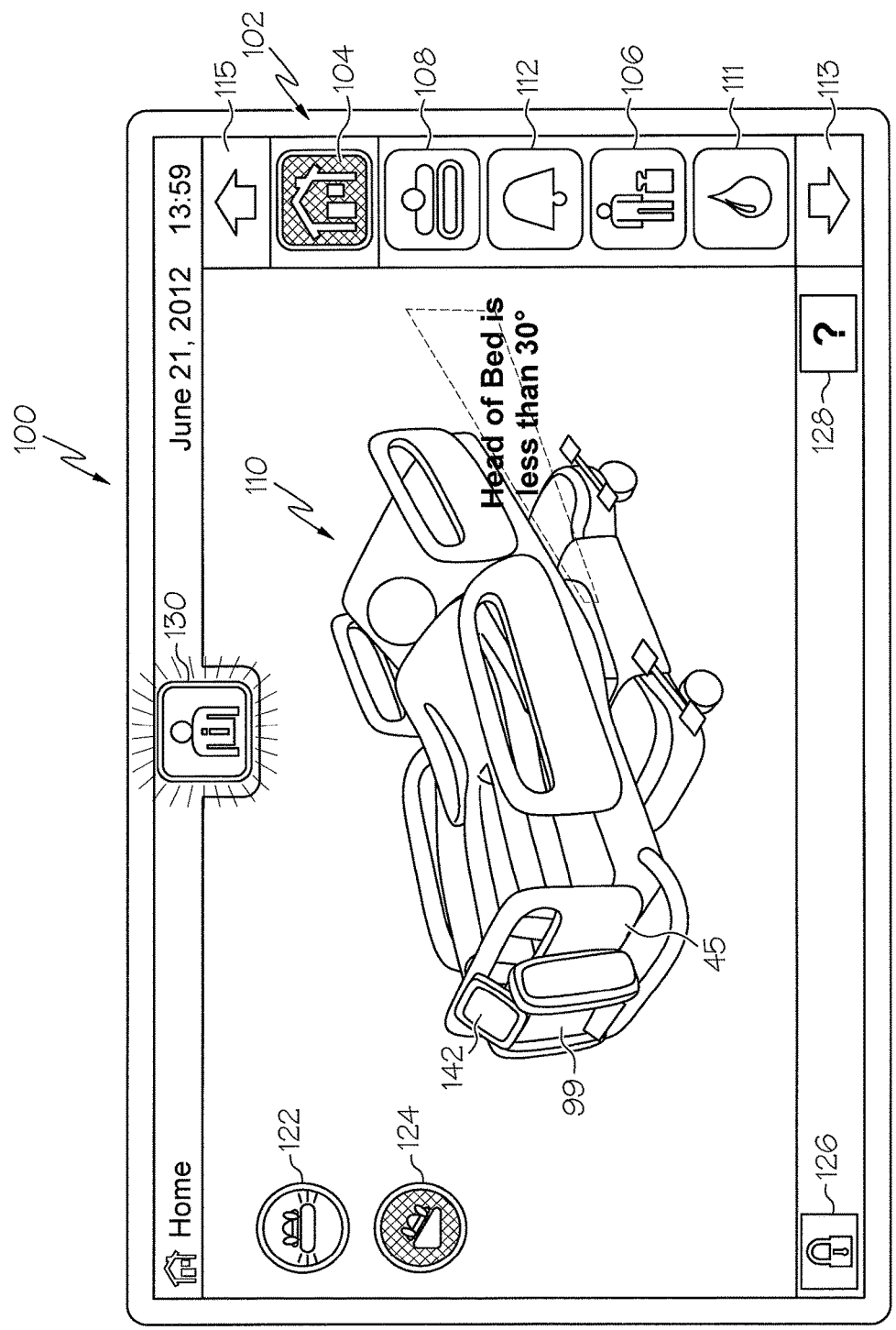
FIG. 5A is a screen shot showing another alternative home screen after a caregiver has attempted to initiate the turn assist function of the bed and showing a patient information icon flashing at the top of the screen.
Figure 5B:
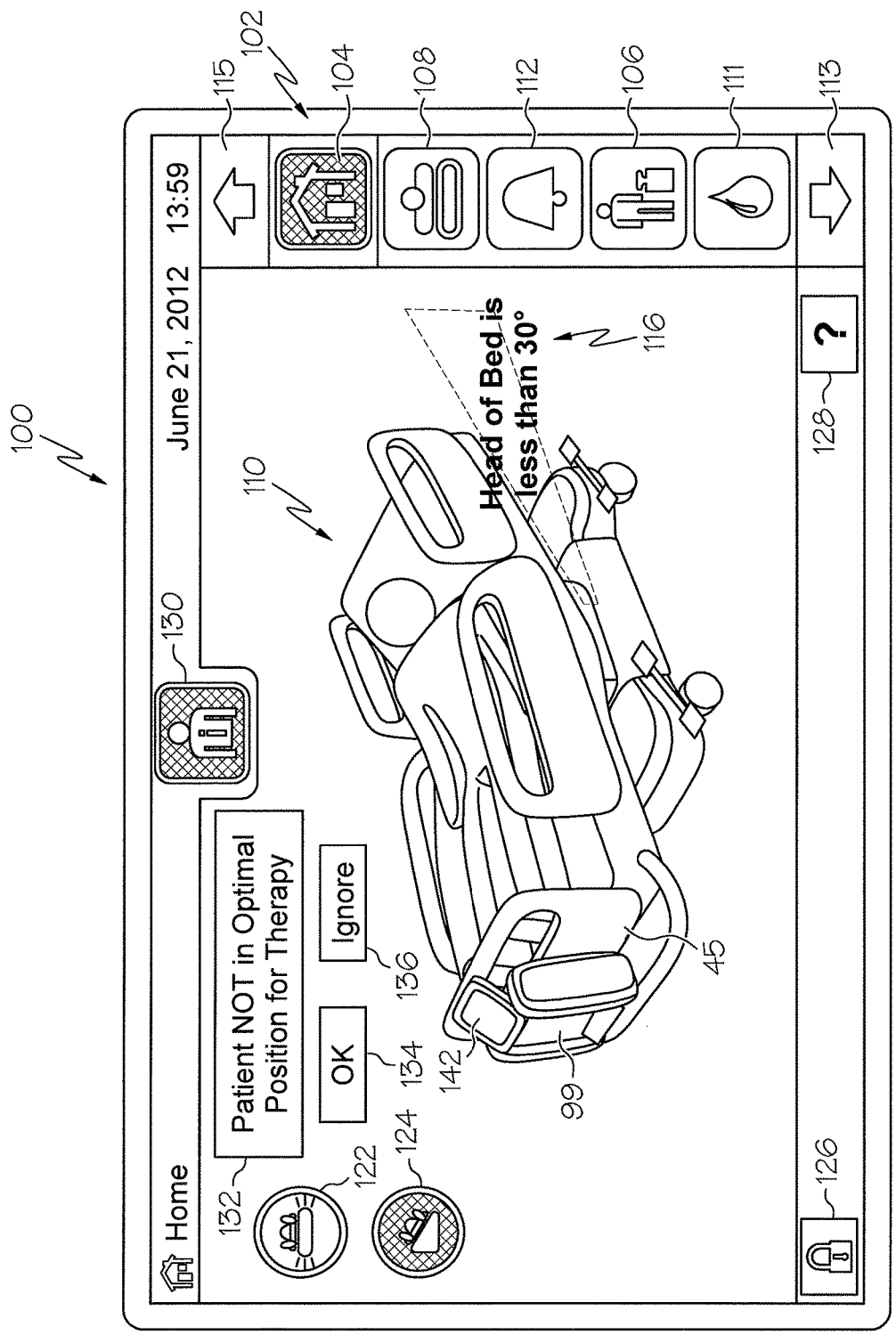
FIG. 5B is a screen shot showing that, after the caregiver selects the patient information icon on the screen of FIG. 5A, the block of text indicating that the patient is not in an optimal position as well as the OK and Ignore icons similar to those of FIG. 4 appear on the screen.

Referring now to FIG. 5A, another alternative home screen 100 is shown after a caregiver has attempted to initiate a therapy function of bed 10. In this variant, the therapy function does not operate and the patient information icon 130 flashes at the top of screen 100. In response to the caregiver selecting the flashing icon 130 on screen 100 of FIG. 5A, the screen 100 of FIG. 5B results and includes text box 132 and icons 134, 136 appearing on screen 100. Icons 134, 136 are used in the same manner as described above to abort the therapy altogether or to override the suspension of the therapy due to the patient being improperly positioned. It should be understood that, even if the caregiver selects icon 136 so that the therapy function or turn assist function proceeds, as the case may be, it is contemplated by this disclosure that one or more caregivers will move the patient to the proper position as the therapy or turn assist function proceeds.

Figure 6A:
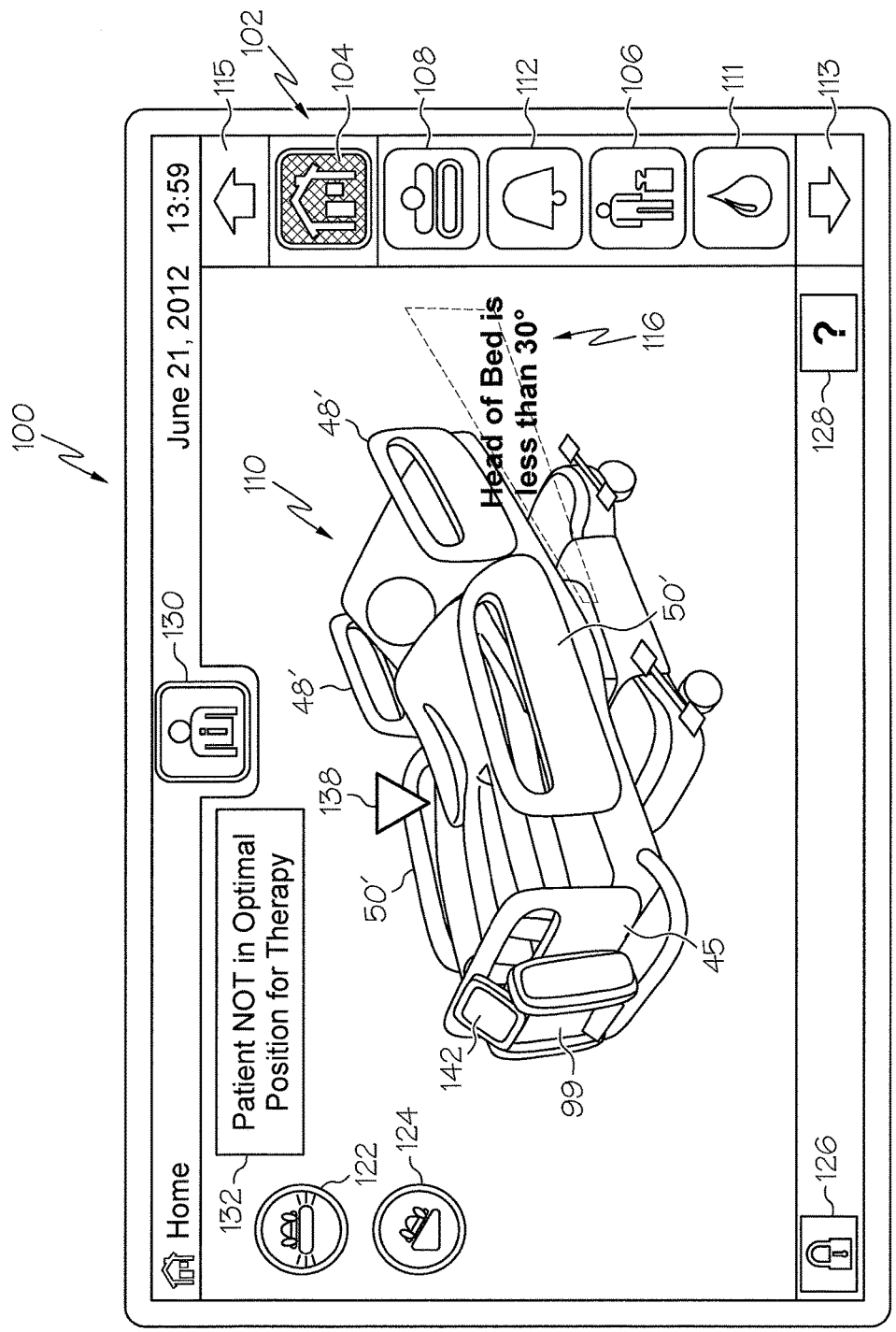
FIG. 6A is a screen shot showing a triangular patient position icon that appears on the home screen at all times and is color coded green, red, or yellow depending upon whether the patient is in the proper position, out of position by a first amount, or out of position by a second amount greater than the first amount.
Figure 6B:
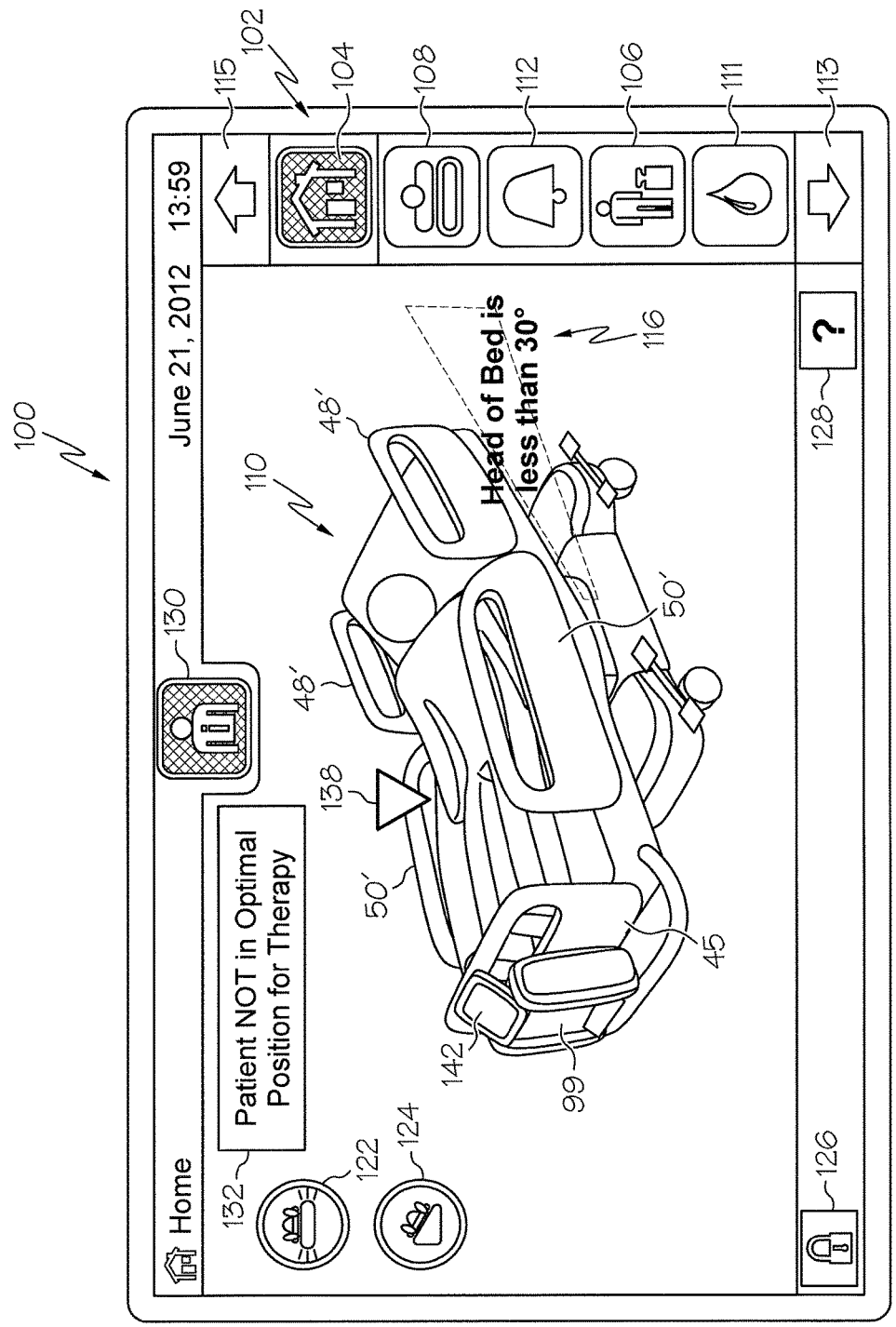
FIG. 6B is a screen shot similar to FIG. 6A, but having the patient information icon shaded to indicate that the triangular patient position icon only appears on the home screen after the patient information icon is selected by a caregiver.

As shown in FIG. 6A, a triangular patient position icon 138 appears on the home screen at all times according to another variant of this disclosure. Icon 138 is color coded green, red, or yellow depending upon whether the patient is in the proper position, out of position by a first amount, or out of position by a second amount greater than the first amount. In the illustrative example, text box 132 also appears on screen 100 along with icon 138 to indicate that the patient is not in the optimal position. Another embodiment is shown in FIG. 6B in which patient information icon 130 is shaded to indicate that the triangular patient position icon 138 and/or text box 132 only appears on the home screen 100 after the patient information icon 138 is selected by a caregiver.

Figure 7:
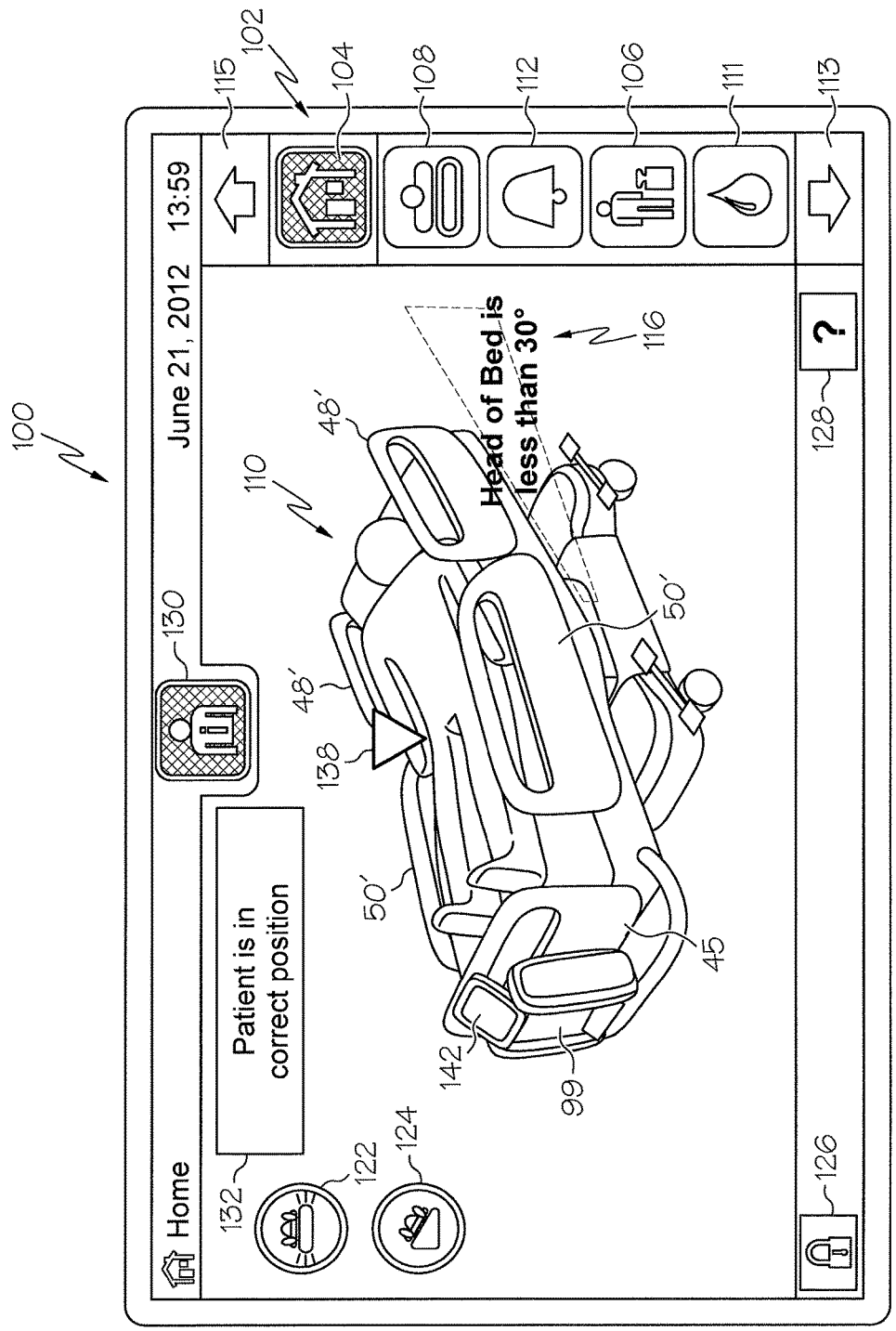
FIG. 7 is an alternative home page screen shot showing that, after the patient position icon is selected when the patient is properly positioned on the bed, a text box appears to indicate that the patient is in the correct position, a triangular hip icon appears to also indicate that the patient is in the correct position, and the patient is represented graphically on the bed in the proper position.

Referring now to FIG. 7, an alternative home page screen 100 is shown in which, after the patient position icon 138 is selected when the patient is properly positioned on the bed, the text box 132 appears and includes the message "Patient is in correct position." Triangular hip icon 138 appears to also indicate that the patient is in the correct position. Furthermore, the patient is represented graphically on the bed in the proper position on icon 110.

Figure 8:
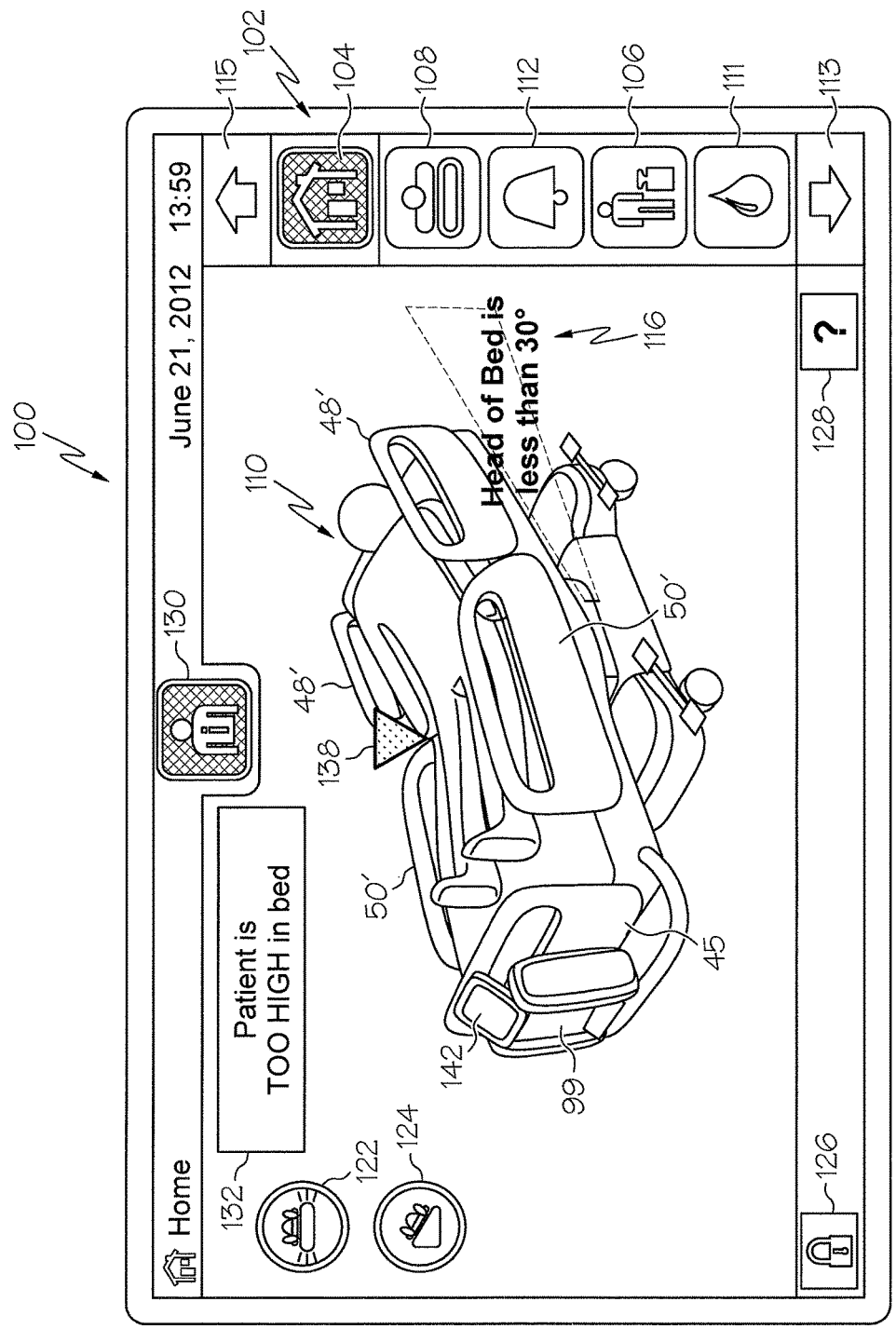
FIG. 8 is a home page screen shot, similar to FIG. 7, showing that, after the patient position icon is selected when the patient is shifted too far toward the head end of the bed, a text box appears to indicate that the patient is too high in the bed, the triangular hip icon is colored to indicate that the patient is not properly positioned in the bed, and the patient is represented graphically on the bed shifted toward the head end of the bed.
Figure 9:
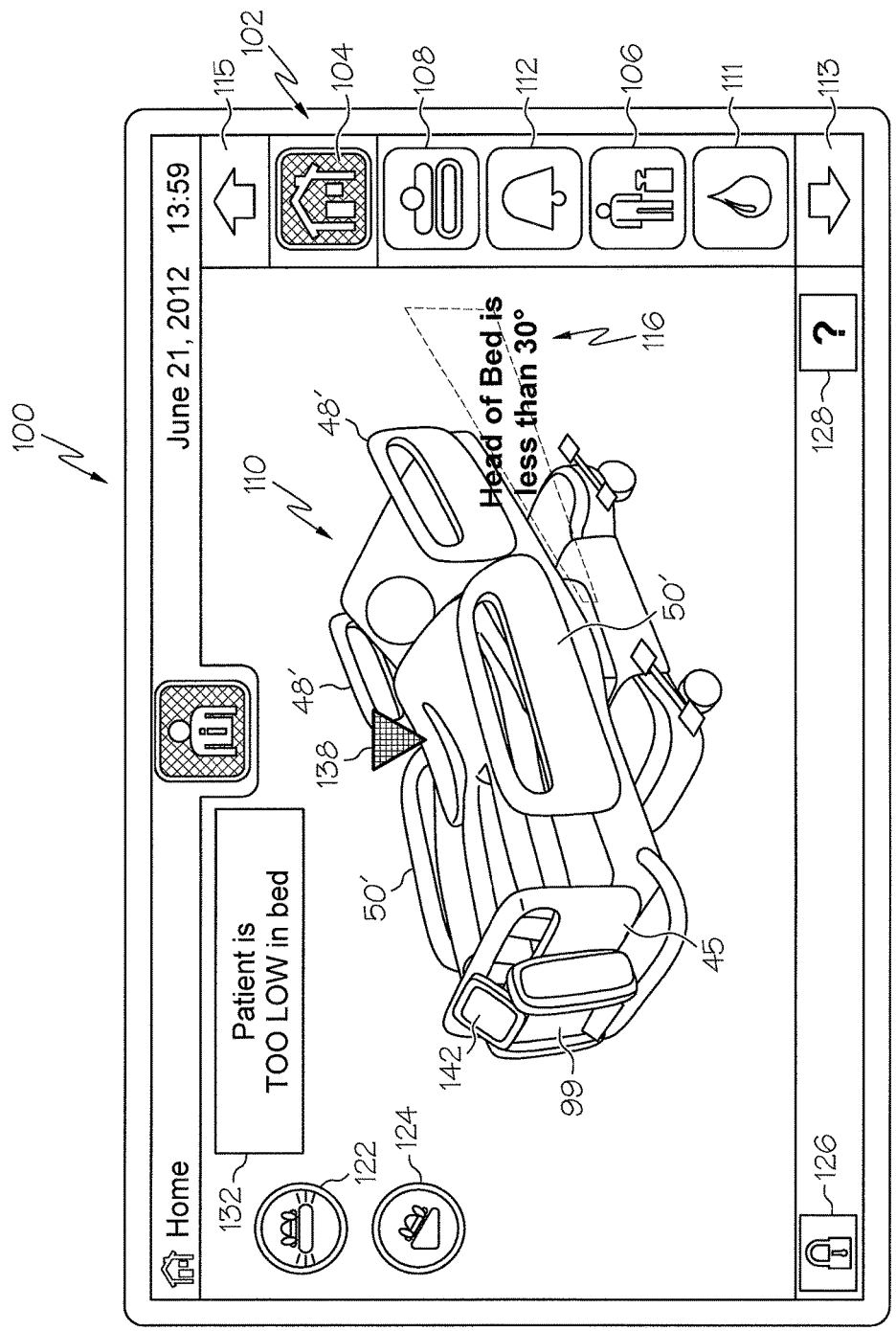
FIG. 9 is a home page screen shot, similar to FIGS. 7 and 8, showing that, after the patient position icon is selected when the patient is shifted too far toward the foot end of the bed, a text box appears to indicate that the patient is too low in the bed, the triangular hip icon is colored to indicate that the patient is not properly positioned in the bed, and the patient is represented graphically on the bed shifted toward the foot end of the bed.

FIG. 8 shows another home page screen shot, similar to FIG. 7, showing that, after the patient position icon 130 is selected when the patient is shifted too far toward the head end of the bed, text box 132 appears with the message "Patient is TOO HIGH in the bed." In the illustrative example, triangular hip icon 138 is colored yellow to indicate that the patient is not properly positioned in the bed by a modest amount. Also, the patient is represented graphically in icon 110 as being shifted toward the head end of the bed 10. FIG. 9 is yet another home page screen shot, similar to FIGS. 7 and 8, showing that, after the patient position icon 130 is selected when the patient is shifted too far toward the foot end of the bed, text box 132 appears with the message "Patient is TOO LOW in the bed." In the illustrative example, triangular hip icon 138 is colored red to indicate that the patient is not properly positioned in the bed by a considerable amount. Also, the patient is represented graphically in icon 110 as being shifted toward the foot end of the bed 10.

According to this disclosure, screens similar or identical to the home page screen shots of FIGS. 8 and 9 appear with text box 132 if the patient has moved too far toward the head end 24 or foot end 26, respectively, regardless of whether a turn assist function or therapy function has been initiated on bed 10. For example, after head section 40 of bed 10 is raised and then lowered back down, there is a tendency for the patient to shift toward foot end 26 of bed 10. In such situations, the screen of FIG. 9 is displayed. In some instances, caregivers assist the patient in moving back toward head end 24 of bed 10 and in other instances, the patient may move themselves back toward the head end 24 of bed 10. However, if the caregivers move the patient too far toward the head end 24 or if the patient moves himself or herself too far toward the head end 24, then the situation will have been overcorrected. In such overcorrection situations, the screen of FIG. 8 is displayed. When the patient is in the proper position, then the home page screen shot of FIG. 7 is displayed.

In some embodiments, screens of FIGS. 7-9 are used during a training mode of bed 10. In the training mode, caregivers practice not pulling a patient too far up in bed 10 after the patient has shifted toward the foot end 26. Such training may be performed using a patient, using another person in lieu of a patient, or using an anthropometric mannequin or the like. In such embodiments, suitable screens are provided for turning off and on the training mode of bed 10.

With regard to sensing the patient's position relative to mattress 22 and/or bed frame 20, there are many possible sensor technologies that may be employed according to this disclosure. Embodiments having a plurality of sensors that provide signals to indicate the position of the patient are contemplated by this disclosure. For example, each sensor of the plurality of sensors may include a load cell, a force sensitive resistor (FSR) element, a piezoelectric material or element, a capacitive sensor, or an optical sensor. If load cells are used, they may include strain gages or capacitors, for example. Such sensors are included as part of scale system 270 in some embodiments. Alternatively or additionally, the patient support surface may have a plurality of patient support bladders and a plurality of sensors, such as pressure sensors or other types of sensors, that may be used to determine a position of the patient on the patient support surface 22 based on signals from the sensors that may be indicative as to which of the plurality of bladders the patient is atop.

U.S. Pat. Nos. 5,276,432 and 7,253,366 provide examples of bed frames having load cells that are used to determine patient position and each of these patents is hereby expressly incorporated by reference herein to the extent that it is not inconsistent with the present disclosure which shall control as to any inconsistencies. U.S. Pat. Nos. 6,208,250 and 7,464,605 provide examples of the use of FSR's to determine patient position and each of these patents is hereby expressly incorporated by reference herein to the extent that it is not inconsistent with the present disclosure which shall control as to any inconsistencies. U.S. Pat. No. 6,067,019 provides examples of the use of capacitive sensors to determine patent position and is hereby expressly incorporated by reference herein to the extent that it is not inconsistent with the present disclosure which shall control as to any inconsistencies. U.S. Pat. No. 6,819,254 provides an example of the use of piezoelectric material to determine patient position and is hereby expressly incorporated by reference herein to the extent that it is not inconsistent with the present disclosure which shall control as to any inconsistencies. U.S. Pat. No. 7,409,735 provides examples of the use of pressure sensors associated with air bladders to determine patient position and is hereby expressly incorporated by reference herein to the extent that it is not inconsistent with the present disclosure which shall control as to any inconsistencies. Some of the other U.S. patents already incorporated by reference herein also include various types of sensors for determining patient position.

While the improper positioning of the patient in the embodiments discussed above was within the context of performing a therapy function or a turn assist function, the present disclosure also contemplates that indications on graphical display screen 142 similar or identical to those in shown in FIGS. 3-9 may alternatively or additionally be displayed in connection with raising head section 40 of frame 20 toward a raised position. The head section 40 is movable in a known manner between a raised position supporting the patient in a sitting up position and a lowered position supporting the patient in a lying down position. It is contemplated that user inputs 66, GUI 142, or both are configured to receive user inputs from a caregiver to initiate the movement of head section 40 between the raised and lowered positions. However, if the patient is improperly positioned on bed 10, such as being slid too far toward the head end 24 or the foot end 26 of frame 20, the GUI 142 is controlled by control circuitry 98 to display information indicating that the patient is improperly positioned on bed 10 for the movement of head section 40 toward the raised position.

In some embodiments, the information indicating that the patient is improperly positioned includes may include one or more of the following: (i) a text box 132 with a message conveying the information, (ii) a pictorial representation 110 of a patient lying on the patient support surface too close to the at least one of the head end and foot end, and (iii) a hip position icon 138 that is color coded. In connection with text box 132, the message states, for example, "Patient NOT in Optimal Position for Raising the Head Section" in lieu of the text shown in the illustrative examples of FIGS. 3, 4, 5B, 6A, and 6B. Similarly, the text shown in FIG. 7 may be included when the patient is properly positioned and the text in box 132 in FIGS. 8-9 may also be included in text box 132 in connection with attempts to raise head section 40 in some embodiments.

In some embodiments, the movement of head section 40 toward the raised position may be suspended until after the caregiver selects first icon 136 on screen 100 of the GUI 142 to ignore the information indicating that the patient is improperly positioned. Alternatively, the movement of head section 40 toward the raised position may be prevented altogether by circuitry 98 until after the patient is moved to a proper position on the patient support structure 10.

As discussed above, bed frame 20 has a plurality of sensors that are part of scale system 270 and that are used to determine a weight of the patient. Some or all of these sensors are also used to determine a position of the patient on the patient support surface 22 and/or frame 20. Frame 20 and surface 22, either individually or together, are considered to be a patient support structure according to this disclosure. It is contemplated that, in some embodiments, the information indicating that the patient is improperly positioned is displayed on the GUI 142 prior to the caregiver using the user inputs 66 to initiate the raising of head section 40. In other embodiments, the information indicating that the patient is improperly positioned is displayed only after an attempt is made to raise head section 40.

In some embodiments, the information regarding whether a patient is or is not properly positioned in connection with raising the head section 40 is only displayed in those instances when head section 40 is below a threshold angle. The threshold angle may be, for example, 30 degrees or 45 degrees or some other angle according to this disclosure. This is because, once the head section 40 has been raised by the threshold amount, the sensors on bed 10 will have readings indicating that the patient has moved too far toward foot end 26 regardless of whether or not the patient is properly positioned. That is, raising the head section 40 shifts the patient's weight toward the foot end 26 of bed 10 even when the patient is properly positioned.

Although certain illustrative embodiments have been described in detail above, many embodiments, variations and modifications are possible that are still within the scope and spirit of this disclosure as described herein and as defined in the following claims.

The invention claimed is:

1. A patient support apparatus comprising
a patient support structure configured to support a patient, the patient support structure having a head end and a foot end spaced apart in a longitudinal dimension of the patient support structure, the patient support structure having a head section that is configured to support a torso of a patient and that is movable between a raised position for supporting the patient in a sitting up position and a lowered position for supporting the patient in a lying down position,
a set of user inputs configured to receive input from a caregiver to initiate the movement of the head section between the raised and lowered positions,
a graphical user interface (GUI) supported by the patient support structure, and
control circuitry coupled to the GUI, the GUI being controlled by the control circuitry to display information indicating, when the patient is lying down on the patient support structure about midway between opposite sides of the patient support structure, that the patient is improperly positioned on the patient support structure in the longitudinal dimension of the patient support structure due to being shifted too far towards the head end or too far towards the foot end for the movement of the head section toward the raised position, wherein the information indicating that the patient is improperly positioned includes all three of the following: (i) a text box with a message conveying the information, (ii) a pictorial representation of a patient lying on the patient support surface too close to the at least one of the head end and foot end, and (iii) a hip position icon that is color coded.

2. The patient support apparatus of claim 1, wherein the movement of the head section toward the raised position is suspended until after the caregiver selects a first icon on the GUI to ignore the information indicating that the patient is improperly positioned.

3. The patient support apparatus of claim 1, wherein the movement of the head section toward the raised position is prevented until after the patient is moved to a proper position on the patient support structure.

4. The patient support apparatus of claim 1, wherein the patient support structure includes a bed frame that includes a siderail and the GUI being mounted to the siderail.

5. The patient support apparatus of claim 1, wherein the patient support structure includes a bed frame having a plurality of sensors, the plurality of sensors are used to determine a weight of the patient, and the plurality of sensors are used to determine a position of the patient on the patient support surface.

6. The patient support apparatus of claim 1, wherein the information indicating that the patient is improperly positioned is displayed on the GUI prior to the caregiver using the user inputs to initiate the raising of the head section.

7. The patient support apparatus of claim 1, wherein the GUI is also controlled by the control circuitry to display information indicating that the patient is properly positioned on the patient support structure.

8. The patient support apparatus of claim 1, wherein the set of user inputs includes a plurality of buttons spaced from the GUI and at least one button of the plurality of buttons is used to initiate movement of the head section toward the raised position.

9. The patient support apparatus of claim 1, wherein the GUI is also controlled by the control circuitry to display information which indicates, when the patient is lying down on the patient support surface about midway between the opposite sides of the patient support structure, that the patient is improperly positioned in the longitudinal dimension of the patient support structure due to being shifted too far towards the head end or too far towards the foot end for at least one of a turn assist function and a therapy function of a mattress supported by the patient support structure.

10. The patient support apparatus of claim 9, wherein the at least one of the turn assist function and the therapy function initiated by the caregiver proceeds automatically despite the improper position of the patient on the patient support structure.

11. The patient support apparatus of claim 9, wherein the at least one of the turn assist function and the therapy function initiated by the caregiver is suspended until after the caregiver selects a first icon on the GUI to ignore the information indicating that the patient is improperly positioned.

12. The patient support apparatus of claim 9, wherein the GUI displays an icon that is selectable by the caregiver to abort the at least one of the turn assist function and the therapy function.

13. The patient support apparatus of claim 1, wherein, before the information indicating that the patient is improperly positioned on the patient support structure is displayed on the GUI, the GUI displays a patient information icon that must be selected by the caregiver.

14. The patient support apparatus of claim 13, wherein the patient information icon flashes on the GUI when the information is being displayed.

15. The patient support apparatus of claim 1, wherein the patient support structure includes a bed frame having a foot board and wherein the GUI is supported on the foot board.

16. The patient support apparatus of claim 1, wherein the patient support structure includes a plurality of patient support bladders and at least one pressure sensor that is used to determine a position of the patient on the patient support surface based on signals from the at least one pressure sensor being indicative as to which of the plurality of bladders the patient is atop.

17. The patient support apparatus of claim 1, wherein the GUI is also controlled by the control circuitry to display information indicating whether the patient is shifted too far towards the head end or too far towards the foot end.

18. The patient support apparatus of claim 1, wherein the hip position icon is triangular.

19. The patient support apparatus of claim 1, wherein the hip position icon is color coded to indicate an amount that the patient is shifted too far towards the head end or too far towards the foot end.

20. The patient support apparatus of claim 19, where in the hip position icon is color coded yellow or is color coded red depending upon the amount that the patient is shifted too far towards the head end or too far towards the foot end.

* * * * *